US00PP07921P

United States Patent [19]

van Andel

[11] Patent Number: Plant 7,921

[45] Date of Patent: Jul. 21, 1992

[54] CARNATION NAMED STAPITROS

[75] Inventor: Jacob van Andel, Aalsmeer, Netherlands

[73] Assignee: Van Staaveren B.V., Aalsmeer, Netherlands

[21] Appl. No.: 583,855

[22] Filed: Sep. 13, 1990

[51] Int. Cl.[5] ..... A01H 5/00

[52] U.S. Cl. ..... Plt./70.5

[58] Field of Search ..... Plt./70, 71, 72

[56] References Cited

U.S. PATENT DOCUMENTS

P.P. 7,413 1/1991 Hilverda ..... Plt. 70

P.P. 7,525 5/1991 Hilverda ..... Plt. 70

*Primary Examiner*—Howard J. Locker

*Attorney, Agent, or Firm*—Charles W. Rummler

[57] ABSTRACT

A new and original mini-spray carnation variety particularly distinguished by its rose-colored blossoms, the petals of which are flecked with ruby red, with the flecks of the petal forming a ring around the middle of each blossom. This carnation blooms intermittently during the Spring, Summer and Fall blooming periods; the plant itself having a vigorous and upright growth habit and a height of about 60 cm.

1 Drawing Sheet

BACKGROUND OF THE NEW PLANT

This new mini-spray carnation cultivar originated as a hybrid seedling developed by me in 1980 at our nursery in Aalsmeer, Holland by crossing two varieties selected from our collection of carnations maintained for breeding purposes at Aalsmeer. This particular seedling was selected for propagation because of its unusual rose-colored, ruby-flecked flower coloration and the overall high quality of the plant growth. Asexual propagation of this selected plant was done by means of cuttings under my direction at Aalsmeer; and propagation of this new plant by cuttings was continued through successive generations to determine whether the novel characteristics of the selected seedling would be retained from generation to generation and its homogeneity could be assured.

This proved to be successful and this mini-spray carnation variety is now being propagated at Aalsmeer.

DESCRIPTION OF THE DRAWING

My new mini-spray carnation cultivar is illustrated by the accompanying full-color photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to The R.H.S. COLOUR CHART published by The Royal Horticultural Society of London, England.

THE PLANT

Origin: Seedling.

Parentage:

*Seed parent.*—Plant No. 83307-1 J (unpatented).

*Pollen parent.*—Plant No. 85396-1 C (unpatented).

Classification:

*Botanic.*—Dianthus hybrid.

*Commercial.*—Mini-spray carnation.

Form: Strong, upright bush with hardly any shoots in the flower stem nodes.

Height: 60 cm, in average.

Main stem:

*Length.*—In average, about 60 cm.

*Growth.*—Vigorous, upright and strong.

*Branching character.*—Hardly any shoots in the flower stem nodes.

Foliage:

*Number of leaves.*—Abundant, varies with season.

*Leaf size.*—About 140 mm long and 6 mm wide at the fifth node.

*Leaf shape.*—Pointed and strongly curled.

*Margins.*—Entire.

*Texture.*—Leathery.

*Color.*—Upper side: Grey-green.

THE BUD

Size: Medium.

*Diameter.*—Averaging about 10 mm.

*Length.*—Averaging about 20 mm.

Shape: Cylindrical.

Calyx:

*Shape.*—Cylindrical.

*Size.*—Averaging 10 mm in width and 25 mm in length.

*Splitting.*—The calyx does not split.

*Aspect.*—Smooth.

Flower stem:

*Character.*—Strong and erect.

*Color.*—Gray-green.

Length.—Averaging about 50 cm.

THE FLOWER

Blooming habit: Intermittent.

Size of flower: Medium.

*Diameter.*—Averaging about 50 mm.

*Depth.*—Averaging about 10 mm.

Borne: Raceme.

Shape:

*When first opening.*—Flat.

*When mature.*—Rounded top face.

Petalage:
*Number of petals.*—Approximately 25-30 in average.
*Texture.*—Soft.
*Appearance.*—Velvety.
*Color.*—Both outer petals and inside petals: Body: 56 D with flecks of 61 A. Base: 56 D. Reverse side: 56 D.
Fragrance: Normal.
Discoloration:
*After full bloom.*—No discoloration.
Persistence: The flowers hang on and dry.
Disease resistance: Resistant to *Fusarium Oxysporum.*
Lasting quality: Averaging about 14 days as a cut flower and 21 days on the plant.

REPRODUCTIVE ORGANS

Stamens:
*Number.*—Few.
*Arrangement.*—Rudimental.
Anthers:

*Size.*—Small.
*Color.*—Beige.
Filaments:
*Length.*—3 to 4 mm.
*Color.*—White.
*Pollen.*—Color: Beige, if present.
Pistils:
*Number.*—1.
Styles:
*Length.*—About 35 mm.
*Color.*—White.
*Stigma.*—Color: White.

I claim:

1. The new and distinctive carnation plant, substantially as herein shown and described, particularly characterized by its rose-colored flowers flecked with a ring of ruby red, and which are produced intermittently and profusely on the strong, upright stems of a vigorously growing bush.

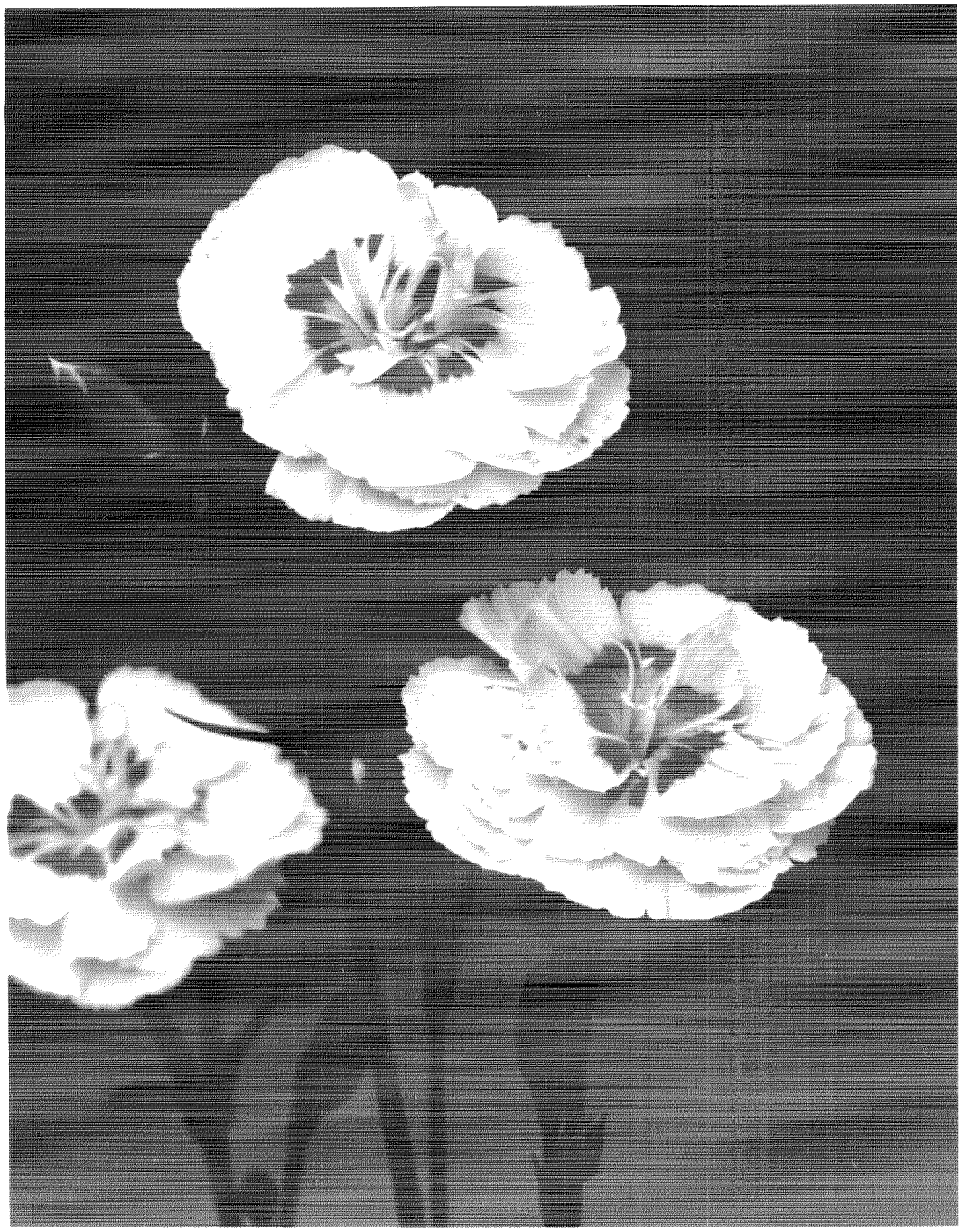

* * * * *